(12) United States Patent
Grundeman et al.

(10) Patent No.: US 8,092,477 B2
(45) Date of Patent: Jan. 10, 2012

(54) DEVICE FOR MAKING A CUT IN A TISSUE

(75) Inventors: Paul Frederik Grundeman, Amsterdam (NL); Hendricus Jacobus Mansvelt Beck, Bilthoven (NL)

(73) Assignee: UMC Utrecht Holding B.V., Utretch (NL)

( * ) Notice: Subject to any disclaimer, the term of this patent is extended or adjusted under 35 U.S.C. 154(b) by 1040 days.

(21) Appl. No.: 10/844,501

(22) Filed: May 13, 2004

(65) Prior Publication Data
US 2005/0256536 A1 Nov. 17, 2005

(51) Int. Cl.
*A61B 17/34* (2006.01)
(52) U.S. Cl. ...................................................... 606/185
(58) Field of Classification Search ................... 606/181, 606/184, 185; 600/583
See application file for complete search history.

(56) References Cited

U.S. PATENT DOCUMENTS

| | | | | |
|---|---|---|---|---|
| 3,007,471 A * | 11/1961 | McClure, Jr. | ................. | 600/567 |
| 3,727,614 A * | 4/1973 | Kniazuk | ........................ | 604/115 |
| 4,299,219 A * | 11/1981 | Norris, Jr. | ...................... | 604/115 |
| 4,660,570 A * | 4/1987 | Dombrowski | ................ | 600/578 |
| 5,314,441 A * | 5/1994 | Cusack et al. | ................. | 606/182 |
| 5,772,677 A * | 6/1998 | Mawhirt et al. | ................ | 606/181 |
| 5,972,013 A * | 10/1999 | Schmidt | ......................... | 606/185 |
| 6,071,249 A * | 6/2000 | Cunningham et al. | ......... | 600/578 |
| 6,086,545 A * | 7/2000 | Roe et al. | ....................... | 600/570 |
| 6,206,841 B1 * | 3/2001 | Cunningham et al. | ......... | 600/584 |
| 6,221,089 B1 * | 4/2001 | Mawhirt | ....................... | 606/181 |
| 6,918,890 B2 * | 7/2005 | Schmidt | ................... | 604/164.01 |
| 7,261,721 B2 * | 8/2007 | Feller | ............................. | 606/133 |
| 2002/0077584 A1 * | 6/2002 | Lin et al. | ......................... | 604/21 |

* cited by examiner

*Primary Examiner* — Ryan Severson
(74) *Attorney, Agent, or Firm* — Young & Thompson

(57) ABSTRACT

A device (1) for making a cut in a tissue, such as a blood vessel (2), capsule and the like, includes a trocar (3), the distal end (4) of which can be placed on the tissue (2) and inside which trocar (3) a reduced pressure can be generated for holding the tissue pressed against the distal end (3) under the influence of the reduced pressure, as well as a cutting member (6) located in the trocar (3), such that the tissue (2) pressed against the distal end (4) and the cutting member (6) can be moved relative to one another to make the cut (9). A tissue support (10) is provided in the trocar (3) close to the distal end (4) thereof with which the tissue (2) that extends over the lumen of the trocar (3) can make contact under the influence of the reduced pressure inside the trocar (3).

8 Claims, 1 Drawing Sheet

DEVICE FOR MAKING A CUT IN A TISSUE

The invention relates to a device for making a cut in a tissue, such as a blood vessel, capsule and the like, comprising a trocar, the distal end of which can be placed on the tissue and inside which trocar a reduced pressure can be generated for holding the tissue pressed against the distal end under the influence of said reduced pressure, as well as a cutting member located in the trocar, such that the tissue pressed against the distal end and the cutting member can be moved relative to one another to make the cut.

Such a device is known. It can, for example, be used for making a cut in a blood vessel in connection with making a bypass. In that case a small tube is sewn around the cut such that the blood flow is able to bypass the constricted section of the blood vessel. In the case of other tissues as well, such as capsules, such a device can be used for making a cut therein.

A tissue such as occurs in a blood vessel is highly elastic. Viewed from inside to outside, it is made up of endothelium, a muscle layer and a collagen skirt. As a consequence of the elasticity, it is difficult to cut through the tissue. It is for this reason that a fairly substantial force has to be exerted on the tissue in order to produce the cut. However, this is problematical, because risks for the surrounding tissue arise as a result. It is desirable to fix the tissue to be treated and then to make the cut by means of a sudden movement.

With the known device the disadvantage arises that the tissue is not fixed well despite being held in contact as a result of the reduced pressure in the trocar. In the region of the lumen of the trocar, which is precisely the region where the cut has to be made, the tissue is able to move, as a result of which the cut can be unsuccessful.

The aim of the invention is therefore to provide a device of the type described above that does not have this disadvantage. Said aim is achieved in that there is a tissue support in the trocar close to the distal end thereof with which the tissue that extends over the lumen of the trocar can make contact under the influence of the reduced pressure inside the trocar.

With the device according to the invention the tissue is held firmly fixed in place in contact with the tissue support. The reduced pressure in the trocar ensures that the tissue is held in contact uniformly and will not shift when the blade comes into contact with it. Depending on the position of the tissue support, the tissue is sucked into the distal end of the trocar to some extent, which provides further stabilisation. In this context, the distance from the tissue support to the distal end of the trocar can be, for example, at most equal to a transverse dimension of the trocar.

In order to make the suction effect on the tissue possible, the tissue support must be permeable to gas. To this end the tissue support can be constructed as a grating or a mesh.

Furthermore, the tissue support has a passageway for the cutting member. According to a first possibility, the cutting member is fixed with respect to the tissue support. In this case the cutting action is obtained when the tissue is sucked onto the tissue support. According to a second possibility, the cutting member is movable with respect to the tissue support. In particular, the cutting member can be movable to and fro transversely to the plane of the tissue support. The tissue is then first of all sucked onto the tissue support, after which the blade is driven through the tissue. A drive can also be provided for moving the cutting member to and fro in a relatively short time span ("firing").

As an alternative, the cutting member can also be movable along the plane of the tissue support. It is also possible to combine both movements, that is to say perpendicularly to and parallel to the tissue support.

The invention will be explained in more detail below with reference to a few illustrative embodiments shown in the figures.

Figure 1:
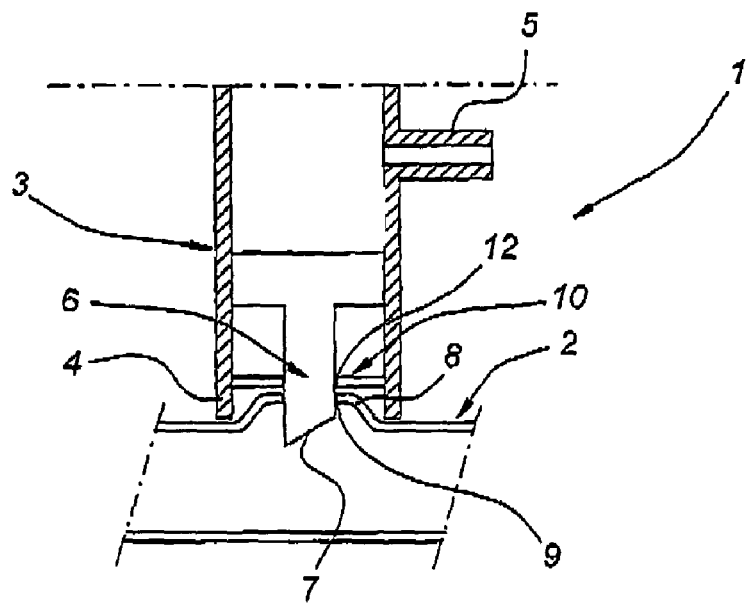
FIG. 1 shows a first illustrative embodiment, in longitudinal section, of a device according to the invention, with blood vessel.

A device 1 according to the invention as applied to a blood vessel 2 in connection with making a cut therein is shown in FIG. 1. The device 1 comprises a trocar 3 with a distal end and a proximal end (not shown). A branch 5, via which a reduced pressure can be generated in the trocar, is joined to the trocar.

Furthermore, there is a blade 6 with an oblique cutting edge oriented downwards in the trocar. The procedure when making a cut is as follows. The distal end 4 of the trocar 3 is placed on the tissue, in the present case the blood vessel 2. A reduced pressure is then generated in the trocar via the branch 5, as a result of which the tissue is sucked into the distal end 4 to some extent. The bulging 8 in the wall of the blood vessel 2 is thus produced. The blood vessel 2 comes into contact with the cutting edge 7 of the blade 6 at this point, such that a cut 9 is obtained in the wall of the blood vessel 2.

Figure 3:
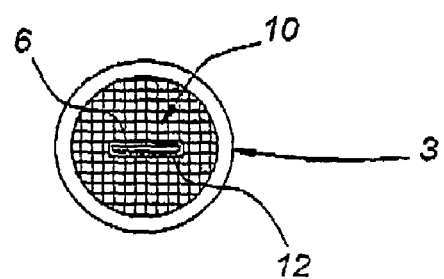
FIG. 3 shows the cross-section according to III-III in FIG. 2.

According to the invention a tissue support 10 is now provided inside the trocar 3, some distance away from the distal end 4. This tissue support, which, for example, can be in the form of the grating or mesh shown in FIG. 3, on the one hand enables a reduced pressure to be produced above the tissue, but, on the other hand, holds said tissue firmly supported, such that the cutting operation can be carried out better.

Figure 2:
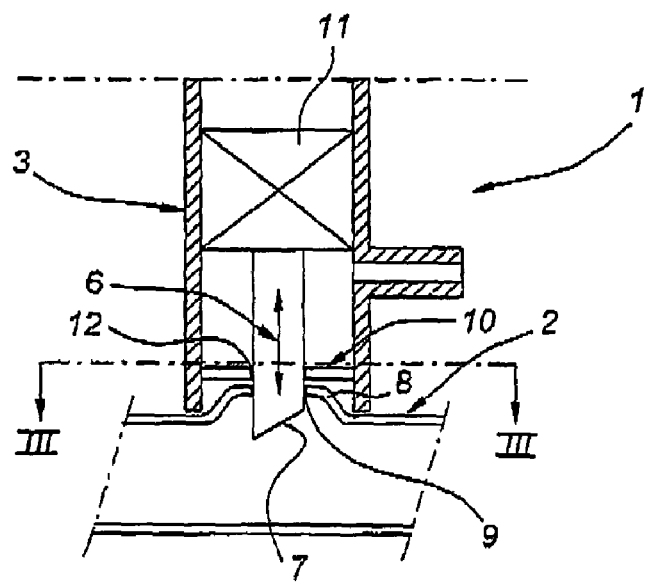
FIG. 2 shows a second illustrative embodiment.

A modified embodiment of the device according to the invention is shown in FIG. 2. With this embodiment the blade 6 with cutting edge 7 can be moved up and down by means of the drive 11, as shown in FIG. 2. At the start of making the cut the blade is in the position in which it has been retracted upwards. After the bulge 8 of the vessel 2 has come into contact with the tissue support 10 as a result of the reduced pressure, the blade 6 is driven through the opening 12 (see FIG. 3) into the vessel wall, as a result of which a very accurate cut is produced.

This cutting operation can take place very rapidly, for example by, as it were, "firing" the blade 6 by means of the drive 11.

The invention claimed is:

1. A device for making a cut in a tissue, comprising:
   a trocar constructed and arranged so that a distal end of the trocar can be placed on the tissue and inside said trocar a reduced pressure can be generated for holding the tissue pressed against the distal end under the influence of said reduced pressure,
   a cutting member located in the trocar, such that the tissue pressed against the distal end and the cutting member can be moved relative to one another to make the cut, and
   a planar tissue support extending transversely over an internal passage of the trocar close to the distal end thereof, with which said tissue support the tissue that extends over the lumen of the trocar can make contact under the influence of the reduced pressure inside the trocar, wherein
   said tissue support comprises one of a grating and a mesh, said grating or mesh having a passageway for the cutting member, and
   the cutting member is moveable to and fro in a direction parallel to the plane of the tissue support.

2. The device according to claim 1, wherein the tissue support is permeable to gas.

3. A device for making a cut in a tissue comprising:
a trocar having a proximal and distal end;
a cutting member located inside the trocar with a cutting edge disposed at the distal end of the trocar; and
a planar tissue support disposed inside and extending transversely over an internal passage of the trocar near the distal end of the trocar;
wherein the tissue support comprises one of a grating and a mesh having a passageway disposed therein through which the cutting member passes, and the cutting member is moveable to and fro in a direction parallel to the plane of the tissue support.

4. The device of claim 3, wherein the tissue support is gas permeable.

5. The device of claim 4, wherein the cutting member is movable to and fro both in a direction along the plane of the tissue support and in a direction transverse to the plane of the tissue support.

6. The device of claim 3, wherein the cutting member is movable to and fro both in a direction along the plane of the tissue support and in a direction transverse to the plane of the tissue support.

7. The device of claim 6, further comprising a drive mechanism for moving the cutting member to and fro.

8. The device of claim 3, further comprising a drive mechanism for moving the cutting member to and fro.

* * * * *